US006855711B1

United States Patent
Warshawsky et al.

(10) Patent No.: US 6,855,711 B1
(45) Date of Patent: Feb. 15, 2005

(54) PHARMACEUTICAL COMPOSITIONS COMPRISING IRON CHELATORS FOR THE TREATMENT OF NEURODEGENERATIVE DISORDERS AND SOME NOVEL IRON CHELATORS

(75) Inventors: Abraham Warshawsky, deceased, late of Rehovot (IL); by Rivka Warshawsky, legal representative, Rehovot (IL); Moussa B. H. Youdim, Haifa (IL); Dorit Ben-Shachar, Kiryat Haim (IL)

(73) Assignees: Yeda Research and Development Co. Ltd., Rehovot (IL); Technion Research and Development Foundation Ltd., Haifa (IL)

( * ) Notice: Subject to any disclaimer, the term of this patent is extended or adjusted under 35 U.S.C. 154(b) by 90 days.

(21) Appl. No.: 10/009,300

(22) PCT Filed: Jun. 7, 2000

(86) PCT No.: PCT/IL00/00332

§ 371 (c)(1),
(2), (4) Date: May 13, 2002

(87) PCT Pub. No.: WO00/74664

PCT Pub. Date: Dec. 14, 2000

(30) Foreign Application Priority Data

Jun. 7, 1999 (IL) .............................................. 130324

(51) Int. Cl.$^7$ .................... A61K 31/165; A61K 31/137; A61K 31/15; A61K 31/47; A61K 31/4709

(52) U.S. Cl. ............................. 514/235.2; 514/253.06; 514/311; 514/547; 514/563; 514/620; 514/655; 544/128; 544/363; 546/165; 546/168; 546/176; 546/179; 560/169; 562/565; 564/165; 564/389

(58) Field of Search ................................. 544/128, 363; 546/165, 168, 176, 179; 560/169; 562/565; 564/165, 389; 514/235.2, 253.06, 311, 547, 563, 620, 655

(56) References Cited

U.S. PATENT DOCUMENTS 4,652,519 A 3/1987 Warshawsky et al. ......... 535/7

FOREIGN PATENT DOCUMENTS

EP 0 329 481 A2 8/1989
JP 63-238060 10/1988

OTHER PUBLICATIONS

Kahana N et al.: "A Conceptual Approach to the Synthesis of Bifunctional EDTA Analogsedta–Extended Polyamides", Journal or Organic Chemistry, US, American Chemical Society, Easton, vol. 59, No. 17, Aug. 26, 1994, pp. 4832–4837, XP000576114.

Warshawsky A.: "Bifunctional Chelating Agents Part 3", J. Chem. Soc. Perkin Trans. I, vol. 10, 1989, pp. 1781–1786 XP002155815.

Hall E D et al. "Neuroprotective Efficacy of Microvascularly–Localized Versus Brain–Penetrating Antioxidants.", Acta Neurochirurgica. Supplementum, (1996) 66 107–13 Ref: 23, XP000972206.

Wesemann, W. (1) et al. "Effect of Lazaroid U–74389G on Iron–Induced Reduction of Striatal Dopamine Metabolism", Journal Of Neural transmission Supplement, (1995) vol. 46, No. 0, pp. 175–182.

Ben–Shachar D et al. "Iron Melanin Interaction and Lipid Peroxidation Implications for Parkinson's Disease" J Neurochem, (1991) 57(5), 1609–1614, XP000972207.

Warshawskky A et al. "Cytotoxicity Effects of Transition–Metal Chelators of the 5–Substituted 2–Hydroxyacetophenones and Their Oximes", European Journal Of Medicinal Chemistry, vol. 30, No. 7–8, 1995, pp. 553–560, XP002163945.

Kirienko, G. K. et al. "Derivatives of 8–Hydroxyquinoline as Possible Anthelmintics, Nematocides, and Fungicides" retrieved from STN, Database accession No. 70:106350 HCA, XP002163950 (1968).

Warner VD et al. "Quantitative Structure Activity Relationships for 5–Substituted 8–Hydroxyquinolines as Inhibitors of Dental Plaque", Journal Of Medicinal Chemistry, (Jan. 1976) 19 (1) pp.92–96. XP002163946.

Warner V D et al. "Synthesis and in Vitro Evaluation of 8–Hydroxyquinoline Analogs as Inhibitors of Dental Plaque" Journal Of Medicinal Chemistry, (Jan. 1976) 19 (1) pp. 167–169.

Burckhalter et al. "Amino and Chloromethylation of 8–Quinolinol–Mechanism of Preponderant Ortho Substitution in Phenols Under Mannich Conditions", Journal Of Organic Chemistry, vol. 26, Oct. 1961 pp. 4078–4083, XP002163948 p. 4078–4083.

Matsumura et al. "Condensation of Chloral Hydrate with 8–Quinolinol", Journal Of The Americal Chemical Society, 1955, pp. 6671–6674, XP002163949.

Primary Examiner—Richard L. Raymond
(74) Attorney, Agent, or Firm—Browdy and Neimark, P.L.L.C.

(57) ABSTRACT

Use of a compound of formula (I), wherein $R^1$ is H or hydrocarbyl; $R^2$ is a hydrophobic radical; $R^3$ is 3-($C_2$–$C_6$) acyl-4-hydroxyphenyl, 3-hydroxyimino ($C_2$–$C_6$)-alkyl-4-hydroxyphenyl, or COOZ, wherein Z is H, ($C_1$–$C_6$) alkyl, aryl, aryl or ar($C_1$–$C_6$) alkyl; and n is 1–20; and of a compound of formula (II), wherein $R^4$ is ($C_1$–$C_6$) alkyl, cyano ($C_1$–$C_6$) alkyl, ($C_1$–$C_6$) alkoxy ($C_1$–$C_6$) alkyl or —$CH_2NR^7R^8$, wherein $R^7$ and $R^8$, the same or different, is each H or ($C_1$–$C_6$) alkyl, or together with the N atom form a saturated or unsaturated 5–7 membered ring optionally containing a further heteroatom selected from N, O or S, the further N atom being optionally substituted, and either $R^5$ is H and $R^6$ is ($C_2$–$C_6$) acyl or hydroxyimino ($C_2$–$C_6$) alkyl, or $R^5$ and $R^6$ together with the phenyl ring form a quinoline, a 1,2,3,4-tetrahydroquinoline or a perhydroquinoline ring, for the preparation of pharmaceutical compositions for the treatment of Parkinson's disease or stroke.

26 Claims, No Drawings

PHARMACEUTICAL COMPOSITIONS COMPRISING IRON CHELATORS FOR THE TREATMENT OF NEURODEGENERATIVE DISORDERS AND SOME NOVEL IRON CHELATORS

REFERENCE TO RELATED APPLICATIONS

The present application is the national stage under 35 U.S.C. 371 of international application PCT/IL00/00332, filed Jun. 7, 2000 which designated the United States, and which international application was published under PCT Article 21(2) in the English language.

FIELD OF THE INVENTION

The present invention relates to pharmaceutical compositions comprising as active ingredients compounds that act as neuroprotective iron chelators and are suitable for the treatment of neurodegenerative disorders such as Parkinson's disease, Alzheimer-type dementia and stroke. The invention further relates to certain novel iron chelators of the type described in the specification.

BACKGROUND OF THE INVENTION

Parkinson's disease is a progressive neurodegeneration of the melanized dopaminergic neurons in the substantia nigra. It is clinically characterized mainly by akinesia, bradykinesia and tremor at rest. Postmortem studies on brains from parkinsonian patients suggest the involvement of oxygen free radical-induced oxidative stress which results in lipid peroxidation of cell membranes, followed by increased membrane fluidity and finally cell death.

Normally dopamine (DA) is metabolized by either monoamine oxidase or by autooxidation. Both ways lead to an excess of toxic oxygen species, such as $H_2O_2$, which in the presence of a transient metal, such as iron, will produce cytotoxic oxygen free radicals, e.g. superoxide and hydroxyl free radicals. The brain, like all other tissues, protects itself against the deleterious effects of oxygen free radicals by specific protective enzymes such as glutathione peroxidase, catalase and superoxide dismutase, and by relatively high amounts of glutathione and ascorbate. In addition, iron is bound to high molecular weight proteins such as ferritin, hemosiderin and transferrin, or to low molecular weight molecules such as ADP, ATP, catechol and probably also melanin, and its amount in the brain is strictly conserved by the blood brain barrier (BBB).

In Parkinson's disease, the brain defensive mechanisms against the formation of cytotoxic oxygen free radicals are defective. In the substantia nigra of parkinsonian brains there are reductions in activities of superoxide dismutase and glutathione peroxidase and reduced tissue contents of glutathione and ascorbate. Moreover, iron concentrations are significantly elevated in parkinsonian substantia nigra pars compacta within the melanized dopamine neurons. These conditions favor liberation of free cytotoxic radicals, which can cause among other things release of intracellular calcium and lipid peroxidation resulting in neuronal death. Indeed an increase in basal lipid peroxidation in the substantia nigra of parkinsonian patients has been detected.

Iron alone or iron decompartmentalized from its binding site by a neurotoxin, e.g. the dopaminergic neurotoxin 6-hydroxydopamine (6-OHDA), may induce oxidative stress and neurodegeneration, as evidenced in previous studies of the inventors in which intranigral administration of iron induced "Parkinsonism" in rats and the iron chelator desferrioxamine protected the rats against 6-OHDA-induced lesions of nigrostrial dopamine neurons (D. Ben-Shachar and M. B. H. Youdim, 1991, J. Neurochem. 56: 1441–4). It has thus been suggested that treatment or retardation of the process of dopaminergic neurodegeneration in the substantia nigra may be affected by iron chelators capable of crossing the blood brain barrier in a fashion similar to chelators used in the treatment of Wilson's disease and iron overload in systemic organs.

This may be a new therapeutic approach for the treatment of Parkinson's disease that can be applied to other metal-associated neurological disorders such as tardive dyskinesia, Alzheimer's and Hallervorden-Spatz diseases.

Stroke is the third leading cause of death in the western world today, exceeded only by heart diseases and cancer. The overall prevalence of the disease is 0.5–0.8% of the population. Stroke is characterized by a sudden appearance of neurological disorders such as paralysis of limbs, speech and memory disorders, sight and hearing defects, etc., which result from a cerebrovascular damage.

Haemorrhage and ischemia are the two major causes of stroke. The impairment of normal blood supply to the brain is associated with a rapid damage to normal cell metabolism including impaired respiration and energy metabolism lactacidosis, impaired cellular calcium homeostasis release of excitatory neurotransmitters, elevated oxidative stress, formation of free radicals, etc. Ultimately these events lead to cerebral cell death and neurological disfunction.

Treatment of stroke is primarily surgical. Much effort is being invested in less aggressive therapeutical intervention in the search for drugs which are capable of restoring normal blood perfusion in the damaged area as well as drugs which are designed to overcome the above listed damaging events associated with cellular damage.

Oxidative stress and free radical formation play a major role in tissue injury and cell death. These processes are catalyzed by transient metal ions, mainly iron and copper. In the case of stroke, since vascular damage is involved, iron is available for the free radical formation, a process that could be prevented by iron chelators. Indeed, with lazaroides (21-amino steroids), known free radical scavengers, a significant improvement of local and global ischemia damages induced in animals has been achieved.

For the treatment of Parkinson's disease and probably other metal-associated neurological disorders and for the treatment of trauma and stroke and the secondary injuries which follow them, it would be highly desirable to find neuroselective iron chelators that cross the blood brain barrier.

SUMMARY OF THE INVENTION

It has now been found in accordance with the present invention that certain iron chelators which can cross the brain blood barrier are able to protect rats from neurodegenerative processes, thus making them suitable candidates for treatment of Parkinson's disease and other metal-associated neurological disorders and for treatment of trauma end stroke.

The present invention relates to the use of a compound selected from the group consisting of:

(a) a compound of formula I:

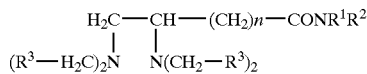

wherein $R^1$ is H or hydrocarbyl; $R^2$ is a hydrophobic radical; $R^3$ is a radical selected from 3-($C_2$–$C_6$)acyl-4-hydroxyphenyl, 3-hydroxyimino($C_2$–$C_6$)alkyl-4-hydroxyphenyl, or COOZ, wherein Z is H, ($C_1$–$C_6$) alkyl, aryl or ar($C_1$–$C_6$)alkyl; and n is an integer from 1 to 20; and (b) a compound of formula II:

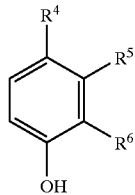

wherein $R^4$ is ($C_1$–$C_6$)acyl, nitro($C_1$–$C_6$)alkyl, cyano($C_1$–$C_6$) alkyl, ($C_1$–$C_6$)alkoxy($C_1$–$C_6$)alkyl or —$CH_2NR^7R9$, wherein R7 and $R^8$, the same or different, is each H or ($C_1$–$C_6$)alkyl, or together with the N atom form a saturated or unsaturated 5–7 membered ring optionally containing a further heteroatom selected from N, O or S, the further N atom in such saturated 5–7 membered ring being optionally substituted by $C_1$–$C_6$ alkyl, $C_1$–$C_6$ acyl, hydroxy-($C_1$–$C_6$)alkyl, ($C_1$–$C_6$) alkoxycarbonyl, and 8-hydroxyquinolin-5-yl-($C_1$–$C_6$) alkyl, and either R5 is H and $R^6$ is ($C_2$–$C_6$)acyl or hydroxyimino ($C_2$–$C_6$)alkyl, or $R^5$ and $R^6$ together with the phenyl ring form a quinoline, a 1,2,3,4-tetrahydroquinoline or a perhydro-quinoline ring, or a pharmaceutically acceptable salt thereof, for the preparation of a pharmaceutical coposition for prevention of lipid peroxidation in the brain of mammals and thus for treatment of neurodegenerative disorders, particularly Parkinson's disease In another embodiment, the invention relates to the use of compounds of formulas I and II above for the preparation of a pharmaceutical composition for treatment of stroke.

The present invention further provides a pharmaceutical composition comprising a pharmaceutically acceptable carrier and a compound of formula I or a pharmaceutically acceptable salt thereof. These compositions are for example useful for prevention of lipid peroxidation in the brain of mammals and thus for the treatment of neurodegenerative disorders such as for treatment of Parkinson's disease, and for treatment of stroke.

The invention further relates to novel compounds of formula I excepting the compounds N-[5-(tert-butoxycarbonyl)pentyl]-4,5-bis[(di(benzyloxycarbonyl) methyl]amino]valeramide, N-(benzyloxy-carbonylaminopropyl)-4,5-bis[(di(methoxycarbonylmethyl) amino]valeramide, N-(benzyloxycarbonylaminopropyl)-4, 5-bis[[di(benzyloxy-carbonylmethyl)amino]valeramide, and N-(benzyloxy-carbonylaminoethyl)-4,5-bis[(di (carboxymethyl)amino]valeramide; to novel compounds of formula II wherein $R^5$ in H and $R^6$ is ($C_2$–$C_6$)acyl or hydroxyimino($C_2$–$C_6$)alkyl, excepting the compounds 2-hydroxy-5-(dipropylaminomethyl)acetophenone and 2-hydroxy-5-(dipropylaminomethyl)acetophenone oxime; and to novel compounds of formula II 1 wherein $R^5$ and $R^6$ together with the phenyl ring foam a quinoline, a 1,2,3,4-tetrahydroquinoline or a perhydroquinoline ring, excluding the quinoline compounds wherein $R^4$ is ($C_1$–$C_2$)acyl, cyanomethyl, ($C_1$–$C_6$)alkoxymethyl or —$CH_2NR^7R^8$, wherein $R^7$ and $R^8$ are both H or ($C_1$–$C_6$)alkyl, or together with the N atom form a saturated ring selected from pyrrolidino, piperidino, morpholino, and piperazino.

In the compounds of formula I, n is preferably 2 to 4, most preferably 2, in which case the compounds are derivatives of valeramide. The term "hydrocarbyl", as used herein for the radical $R^1$, refers to hydrocarbyl radicals that are saturated, unsaturated or aromatic, including, but not being limited to, $C_1$–$C_8$ alkyl, e.g. methyl, ethyl, propyl and butyl, $C_2C_8$ alkenyl, e.g. vinyl and allyl, and phenyl.

The term "hydrophobic" radical, as used herein for $R^2$, includes, but is not limited to, radicals such as $C_6$–$C_{20}$ alkyl; $C_6$–$C_{20}$ alkenyl; a radical selected from $C_5$–$C_{20}$ acyl, benzyloxycarbonyl, substituted benzyloxycarbonyl, $C_3$–$C_8$ alkoxycarbonyl, cycloalkoxycarbonyl, and aryloxycarbonyl, said radical being either linked directly to the N atom or through a ($C_1$–$C_5$)alkylene chain; and N-substituted amino or 4-substituted-piperazino linked to the N atom through a ($C_1$–$C_5$)alkylene chain.

Illustrative examples of hydrophobic radicals for $R^2$ include, but are not limited to, the following; $C_6$–$C_{20}$ straight or branched alkyl or alkenyl such as hexyl, octyl, dodecyl, undecyl, dodecyl and the corresponding alkenyl radicals; a saturated or unsaturated $C_5$–$C_{20}$ carboxylic acyl group such as, for example, an alkanoyl radical selected from hexanoyl, octanoyl, lauroyl, palmitoyl, myristoyl, stearoyl and aracidyl, and the corresponding alkenoyl radicals, linked directly to the N atom or through a ($C_1$–$C_5$) alkylene chain; benzyloxycarbonyl or halo-substituted benzyloxycarbonyl, e.g. o- and p-chloro-benzyloxycarbonyl, 2,4- and 2,6-dichlorobenzyloxycarbonyl, linked directly to the N atom or through a ($C_1$–$C_5$)alkylene chain; a bulky alkoxycarbonyl group such as tert-butoxycarbonyl (Boc), tert-amyloxycarbonyl, isopropoxycarbonyl, linked directly to the N atom or through a ($C_1$–$C_5$)alkylene chain, e.g. tert-butoxycarbonylpentyl; cycloalkoxycarbonyl, e.g. cyclopentoxycarbonyl, cyclohexyloxycarbonyl, adamantyloxycarbonyl (Adoc), linked directly to the N atom or through a ($C_1$–$C_5$) alkylene chain; aryloxycarbonyl such as fluorenylmethoxycarbonyl, linked directly to the N atom or through a ($C_1$–$C_5$)alkylene chain; 4-substituted-piperazinyl or N-substituted amino, linked to the N atom through a ($C_1$–$C_5$)alkylene chain, wherein the 4- and N-substituent is a hydrophobic group such as $C_6$–$C_{20}$ alkyl, $C_6$–$C_{20}$ alkenyl, $C_5$–$C_{20}$ acyl, benzyloxycarbonyl, substituted benzyloxycarbonyl, $C_3$–$C_8$ alkoxycarbonyl, cycloalkoxycarbonyl, aryloxycarbonyl, N-substituted amino and 4-substituted-piperazinyl, all such substituents being as defined above.

The radical $R^3$ in the compounds of formula I may be a group 3-($C_2$–$C_6$)acyl-4-hydroxyphenyl, in which the $C_2$–$C_6$ carboxylic acyl may be acetyl, propionyl, butyryl, hexanoyl; a group 3-hydroxyimino($C_2$–$C_6$)alkyl-4-hydroxyphenyl, in which the alkyl may be ethyl, propyl, butyl, hexyl; or a group COOZ in which Z is H, $C_1$–$C_6$ alkyl, e.g. methyl, ethyl, propyl, butyl, pentyl, and hexyl, aryl, e.g. phenyl, or aralkyl, such as benzyl.

In preferred embodiments of the invention in the compounds of formula I, n is 2, $R^1$ is H and $R^2$ is a radical —$(CH_2)_3NHCOOCH_2C_6H_5$, 5-(tert-butoxycarbonyl)pentyl, or —$(CH_2)_2$-(4-carbobenzoxy)piperazinyl, and $R^3$ is benzyloxycarbonyl, 3-(1-hydroxy-iminoethyl)-4-hydroxyphenyl or 3-acetyl-4-hydroxyphenyl. Examples are the compounds of formula I identified as Compounds 1–4 in the Appendix A just before the claims.

The compounds of formula II in which $R^5$ is H and $R^6$ is $(C_2-C_6)$acyl or hydroxyimino$(C_2-C_6)$alkyl represent keto derivatives of phenol and their corresponding oximes. The acyl is preferably $C_2-C_6$ saturated aliphatic acyl, such as, for example, acetyl, propionyl, butyryl, hexanoyl; and the $(C_2-C_6)$alkyl is for example, ethyl, propyl, butyl, pentyl.

In the compounds of formula II, $R^4$ may be $C_1-C_6$ acyl, such as, for example, formyl, acetyl, propionyl, butyryl, caproyl; nitro$(C_1-C_6)$alkyl, in which the $(C_1-C_6)$alkyl group may be branched, such as, for example, 2-methyl-2-nitropropyl; cyano$(C_1-C_6)$alkyl, e.g. cyanomethyl, cyanopropyl; $(C_1-C_6)$alkoxy$(C_1-C_6)$alkyl, such as, for example, methoxymethyl, ethoxymethyl; $CH_2NR^7R^8$, in which $R^7$ and $R^8$ are both H, or one is H and the other is $C_1-C_6$ alkyl, or both $R^7$ and $R^8$ are alkyl, such as, for example the radical $CH_2NR^7R^8$ may be aminomethyl, methylaminomethyl, ethylaminomethyl, dimethyl-aminomethyl, diethylaminomethyl, or $R^7$ and $R^8$ together with the N-atom form a saturated or unsaturated 5–7 membered ring optionally containing a further heteroatom selected from N, O or S, the further N-atom in such saturated 5–7 membered ring being optionally substituted by $C_1-C_6$ alkyl, e.g. methyl, ethyl, propyl, isopropyl, butyl; $C_1-C_6$ acyl, e.g. formyl, acetyl, propionyl; hydroxy-$(C_1-C_6)$alkyl, e.g. hydroxymethyl, hydroxyethyl, hydroxypropyl; $(C_1-C_6)$ alkoxycarbonyl, e.g. methoxycarbonyl, ethoxycarbonyl, tert-butoxycarbonyl; and 8-hydroxyquinolin-5-yl$(C_1-C_6)$ alkyl, for example, 8-hydroxyquinolin-5-yl-methyl. For example, $R^4$ as a radical $CH_2NR^7R^8$ may be piperidinomethyl, morpholinomethyl, thiomorpholinomethyl, piperazinomethyl, 4-methylpiperazinomethyl, 4-(2-hydroxyethyl)piperazinomethyl, 4-formylpiperazinomethyl, 4-(ethoxycarbonyl)-piperazinomethyl, 4-(butoxycarbonyl)piperazinomethyl, 4-(8-hydroxyquinolin-5-yl-methyl)-piperazinomethyl, 4-(8-hydroxy-quinolin-5-yl- methyl)homopiperazinomethyl, and imidazolylmethyl.

In a preferred embodiment, the compounds of formula II are phenol derivatives as represented by the Compounds 5 and 6 in the Appendix A just before the claims.

In another preferred embodiment, the compounds of formula II are 8-hydroxyquinoline derivatives as represented by the Compounds 7, 9–17, 19–21, 23–26 in the Appendix A just before the claims, preferably the Compound 15.

The compounds of the invention are prepared by chemical synthesis methods well known in the art. Some of these methods are illustrated herein in the Examples. For the preparation of other compounds of formulas I and II, similar procedures known to those of skill in the art may be used.

The compounds of formulas I and II were found according to the present invention to prevent lipid peroxidation in brain homogenates in vitro.

The present invention thus provides pharmaceutical compositions, useful to prevent lipid peroxidation in the brain of mammals comprising a compound of formula I herein or a pharmaceutically acceptable salt thereof, in combination with a pharmaceutically acceptable carrier.

The pharmaceutically acceptable salts according to the invention may be salts formed with compounds of formula I wherein $R^3$ is COOH or are addition salts formed by reaction with inorganic acids such as hydrochloric, hydrobromic, sulfuric or phosphoric acids, or with organic acids such as acetic, propionic, maleic, fumaric, benzoic, citric, tartaric, or oxalic acids, by methods well-known in the art.

In another aspect, the present invention provides the use of a compound of formula I or II herein or of a pharmaceutically acceptable salt thereof as neuroprotective iron chelators for the preparation of pharmaceutical compositions to prevent lipid peroxidation in the brain of mammals and, thus, for the treatment of neurodegenerative diseases such as Parkinson's disease, and for the treatment of stroke.

In still another aspect, the invention relates to a method for the treatment of neurodegenerative diseases such as Parkinson's disease, or for the treatment of stroke, which comprises administering to an individual in need thereof an effective amount of a compound of formula I or of formula II or of a pharmaceutically acceptable salt thereof.

DETAILED DESCRIPTION OF THE INVENTION

The iron chelator compounds I and II of the pharmaceutical compositions of the invention are useful for the treatment of Parkinson's disease and probably other metal-associated neurological disorders and for the treatment of trauma and stroke and the secondary injuries which follow them, by virtue of their ability to cross the blood brain barrier and to prevent lipid peroxidation in the brain, a process which leads to neuronal death.

The ability of the compounds of the invention to prevent lipid peroxidation in brain tissue was first screened in rat brain homogenates in vitro by a method involving the detection of free radicals performed by metabolism of thiobarbituric acid (TBA) to malondialdehyde (MDA) and measurement of the MDA formation, as described by D. Ben-Shachar et al. (1991) J. Neurochem. 57: 1609–14. In this method, brain cortex homogenates are prepared in sucrose and incubated alone to determine basal lipid peroxidation, or incubated after the addition of $Fe_2(SO_4)_3$ or $FeCl_3$ for Fe-induction of maximum free-radical formation, and in the presence of the iron chelators to be tested. After addition of TBA, lipid peroxidation is assayed by measurement of MDA formation.

The ability of iron chelators to act as neuroprotectors was first demonstrated in an animal model of Parkinson's disease (intraventricular injection of 6-hydroxydopamine (6-OHDA)) using the iron chelator desferrioxamine (D. Ben-Shachar et al. (1991) J. Neurochem. 56: 1441–44). A selective increase in content of iron in the pars compacta of the substantia nigra has been implicated in the biochemical pathology of Parkinson's disease. Iron is thought to induce oxidative stress by liberation of oxygen free radicals from $H_2O_2$. Because 6-OHDA is thought to induce nigrostriatal dopaminergic neuronal lesions via metal-catalyzed free radical formation, the effect of the iron chelator desferrioxamine was investigated on 6-OHDA-induced dopaminergic neuron degeneration in the rat. Intracerebroventricular injection of 6-OHDA (250 μg) caused a 88, 79 and 70% reduction in striatal tissue content of dopamine (DA), 3-4-dihydroxyphenylacetic acid (DOPAC) and homovanillic acid (HVA), respectively and a 2.5-fold increase in DA release as indicated by the HVA/DA ratio. Prior injection of desferrioxamine (130 ng and 13 ng, i.c.v.) resulted in a significant protection (~60% and 100%, respectively) against the 6-OHDA-induced reduction in striatal DA content and a normalization of DA release Dopaminergic-related behavioral responses, such as spontaneous movements in a novel environment and rearing, were significantly impaired in the 6-OHDA-treated group. By contrast, the desferrioxamine-pretreated rats exhibited almost normal behavioral responses. The ability of iron chelators to retard dopaminergic neurodegeneration in the substantia nigra indicates a new therapeutic strategy in the treatment of Parkinson's disease.

According to the present invention, compounds of formulas I and II were injected to rats as described in D. Ben-Shachar et al. (1991) J. Neurochem. 56: 1441–44 and were shown to efficiently prevent the 6-OHDA-induced reduction in striatal dopamine and DOPAC concentrations in the rat.

For preparing the pharmaceutical compositions of the present invention, methods well-known in the art can be used. Inert pharmaceutically acceptable carriers can be used that are either solid of liquid. Solid form preparations include powders, tablets, dispersible granules, capsules, cachets and suppositories.

A solid carrier can be one or more substances which may also act as diluents, flavoring agents, solubilizers, lubricants, suspending agents, binders, or tablet disintegrating agents; it can also be an encapsulating material.

Liquid pharmaceutical compositions include solutions, suspensions, and emulsions. As an example, water or water-propylene glycol solutions for parenteral injection may be mentioned. Liquid preparations can also be formulated in solution in aqueous polyethylene glycol solution. Aqueous solutions for oral use can be prepared by dissolving the active component in water and adding suitable colorants, flavoring agents, stabilizers, and thickening agents as desired. Aqueous suspensions for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical composition is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vial or ampoules. The unit dosage form can also be a capsule, cachet, or table itself or it can be the appropriate number of any of these packaged forms.

In therapeutic use for the treatment of Parkinson's disease, the compounds utilized in the pharmaceutical method of this invention may be administered to the patient at dosage levels of from 1 mg/Kg to 20 mg/Kg per day.

In therapeutic use for the treatment of stroke one or more dosages of from about 100 mg/Kg to about 500 mg/Kg of body weight may be administered to the patient as soon as possible after the event.

The dosage, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLES

The formulas of the compounds of Examples 1–26, herein designated Compounds 1–26, are presented in Appendix A, shown just before the Claims.

Example 1

Synthesis of N-[2-(4-carbobenzoxypiperazin-1-yl) ethyl]-4,5-bis[bis(benzyloxycarbonylmethyl)amino] valeramide (1)

To a solution containing N-[2-(4-carbobenzoxypiperazin-1-yl(ethyl]-5-diaminovaleramide (100 mg, 0.27 mmol) in 1 ml $CH_3CN$ (freshly distilled over $P_2O_5$) a mixture of tetramethylnaphthalene-1,8-diamine (0.306 g, 1.43 mmol) and NaI (0.021 g, 0.14 mmol) in 0.12 m n freshly distilled $CH_3CN$ was added. The mixture was heated slightly and stirred under a nitrogen atmosphere to dissolve all components, benzyl 2-bromoacetate was added thereto (0.22 ml, 0.328 g, 1.43 mmol), and the mixture was refluxed at 96° C. for 22 h under a nitrogen atmosphere.

Subsequently, the precipitate was filtered off and the solvent evaporated. $CHCl_3$ was then added to the filtrate, the solid filtered off once again, and the solvent evaporated.

To remove excess benzyl bromoacetate, the residual oil was then washed a few times with hexane, and finally dried under vacuum to yield 300 mg crude product. The product was then purified by flash chromatography, using $CHCl_3$:MeOH as the eluent. 47 mg of the title product were obtained. No further purification was carried out.

Example 2

Synthesis of N-(3-benzyloxycarbonylaminopropyl)-4,5-bis[bis(3-acetyl-4-hydroxybenzyl)amino] valeramide (2)

A suspension of 2-acetyl-4-chloromethylphenol (0.48 g; 2.6 mmol), N-(3-benzyloxycarbonylaminopropyl)-4,5-diamino-valeramide (0.14 g; 0.43 mmol), diisopropyl(ethyl) amine (0.47 ml; 2.96 mmol) in DMF (10 ml) was stirred at room temperature for 24 h. The mixture was evaporated to dryness. $CHCl_3$ (80 ml) was added to the residue, the reaction mixture was filtered off and the solvent was evaporated. The oil was purified by flash chromatography on silica gel using 1% MeOH/$CHCl_3$ as the eluent to receive the pure title product (0.152 mg; 38%). TLC (2% MeOH/$CHCl_3$), $R_f$=0.22.

Example 3

Synthesis of N-(3-benzyloxycarbonylaminopropyl)-4,5-bis[bis(3-(1-hydroxy-iminoethyl)-4-hydroxybenzyl)amino]valeramide (3)

A suspension of Compound 2 of Example 2 (0.55 g; 0.06 mmol), $NH_2OH.HCl$ (0.042 g; 0.6 mmol) and $NaHCO_3$ (0.055 g; 0.065 mmol) in MeOH (15 ml) was stirred at 65° C. for 48 h. $CHCl_3$ (50 ml) was added to the reaction mixture. The precipitate was filtered off, the solvent was evaporated, and the residue was purified by flash chromatography on silica gel using $CHCl_3$ and 5% MeOH/$CHCl_3$ as the eluents. 12 mg (20%) of the title product was eluted with 10% MeOH/$CHCl_3$. The product is not soluble in $CHCl_3$. TLC (10% MeOH/$CHCl_3$). $R_f$=0.15.

Example 4

Synthesis of N-[5-(tert-butyloxycarbonyl)pentyl]-4,5-bis[(bis(benzyloxycaxbonyl)methyl]amino] valeramide (4)

N,N,N',N'-Tetramethylnaphthalene-1,8-diamine (2.18 g; 10.2 mmol) and NaI (0.15 g; 1 mmol) were added to a solution of N-[5-(tert-butyloxycarbonyl)pentyl]-4,5-diaminovaleramide (described in Kahana et al., (1994) J. Org. Chem., Vol. 59, 4832–37) (0.58 g; 1.9 mmol) in $CH_3CN$ (freshly distilled on 3 ml $P_2O_5$) and the reaction mixture was placed in a silicon oil bath at 95° C. Benzyl 2-bromoacetate (1.6 ml; 10.2 mmol) was added, and the mixture was refluxed under N2 for 42 h and then cooled to room temperature. The solid was filtered off and washed with $CHCl_3$. The filtrate and washing were evaporated, and the residual oil was washed (×3) with ethyl acetate/hexane (1:9) to remove excess benzyl bromoacetate. The solvent was decanted and the residue (2.14 g, brown oil) was flash chromatographed on silica gel using 0.25% $MeOH/CHCl_3$ as eluant to give the title product as a yellow-brown oil (0.38 g, 22% yield).

Example 5

Synthesis of 2-acetyl-4-[4-(2-hydroxyethyl) piperazin-1-yl-methyl]phenol (5)

2-Piperazin-1-yl-ethanol (260 mg, 2 mmol) and 2-acetyl-4-chloromethyl phenol (368 mg, 2 mmol) were stirred in chloroform at room temperature. Sodium carbonate (106 mg, 1 mmol) was added and the reaction mixture was stirred overnight. The solid was filtered off and the organic layer washed with water followed by brine, dried over sodium sulfate, filtered and evaporated to obtain the crude product, which was crystallized from ethyl acetate-hexane to receive the title product as yellowish-white crystals (400 mg 72%), mp=72–75° C. $C_{15}H_{22}N_2O_3$ requires: N 10.06 found: N 9.70.

$^1$NMR: d $(CDCl_3)$=12.22 (S, 1H, PhOH), 7.65 (d, 1H, J=1.99 Hz, Ph); 7.445 (dd, 1H, $J_1$=8.62 Hz, $J_2$=2.18 Hz, Ph); 6.94 (d, 1H, J=8.48 Hz, Ph); 3.62 (t, 2H, J=5.25 Hz, $CH_2OH$); 3.46 (S, 2H, $PhCH_2$); 2.65 (S, 3H, $COCH_3$); 2.57–2.41 (m, 11H, $CH_2$×5+OH).

Example 6

Synthesis of 2-(1-hydroxyiminoethyl)-4-[4-(2-hydroxyethyl)piperazin-1-ylmethyl]phenol (6)

Hydroxylamine hydrochloride (63 mg, 0.9 mmol) and sodium bicarbonate (76 mg, 0.9 mmol) were dissolved in distilled water (1 ml). 2-Acetyl-4-[4-(2-hydroxyethyl)-piperazin-1-yl-methyl]phenol (85 mg, 0.3 mmol) in absolute methanol (2 ml) was added and the reaction mixture was stirred at 65° C. for 24 h. $CHCl_3$ (20 ml) was then added, the organic phase washed with water followed by brine, dried over $Na_2SO_4$, filtered and evaporated to obtain the title product (52 mg, 81%).

$^1$NMR: d $(CDCl_3)$=7.36 (d, 1H, J=1.94 Hz, Ph); 7.15 (dd, 1H, $J_1$=2.0 Hz, $J_2$=8.29 Hz, Ph); 6.87 (d, 1H, J=8.28 Hz, Ph); 3.65 (t, 10H, J=5.4 Hz, $CH_2$×5+1H, OH); 2.31 (S, 3H, $CH_3$)

Example 7

Synthesis of 5-formyl-8-hydroxyquinoline (7)

The title compound is prepared in two steps:
7.1 5-(2,2,2-trichloro-1-hydroxyethyl)-8-hydroxyquinoline (8)

To trichloracetaldehyde (41.6 g; 0.28 mol) was added con. $H_2SO_4$ (1 drop) and the mixture was mixed. This chloral was decantated (without the acid) into 8-hydroxyquinoline (27.17 g; 0.187 mol). The reaction was exotermic. After a few minutes of mixing, the reaction mixture was left standing for 3 days at room temperature until it turned to a light yellow solid, and then stirred at 65–70° C. in silicon oil bath for 35 h. After cooling, the reaction mixture was stirred with 3N HCl (470 ml; 140 ml 32% HCl+water . . . 470 ml) at 80° C. for 1.5 h (using mechanical stirrer) until the orange reaction mass completely turned to yellow crystalline hydrochloride, which was filtered after cooling. The crystals were suspended in hot water (375 ml) and sodium acetate trihydrate (75 g; 0.55 mol) was added to the suspension. The mixture was stirred on a water bath (80° C.) for 30 min. The resulting orange-yellow free base was filtered after cooling and washed with hot water and dried under high vacuum with $P_2O_5$. Yield –44.0 g (80%) (from Bull. Chem. Soc. Jp. 42:1741 (1969).
7.2 5-Formyl-8-hydroxyquinoline (7)

Analytic acetone (220 ml) was added to a 3-necked flask equipped with mechanical stirrer which was placed in dry ice-acetone bath, under Ar. Na (4.5 g: 0.2 mol) was added to the cooled acetone during 30 min, then 5-chloralyl-8-hydroxyquinoline (Compound 8) (12.0 g; 0.041 mol) was added to the acetone suspension and the resulting mixture was stirred for 2–3 h at 25° C. After standing for 3 days at room temperature, the resulting precipitate was filtered in buchner, washed with acetone and dried by air. Then the precipitate was dissolved in water (100 ml) and was treated by charcoal (2 teaspoons). After filtration, the solution was neutralized with a 50% solution of $CH_3CO_2H$ (few drops). A straw yellow precipitate was filtered (mother solution 1) and dried in a desiccator over $P_2O_5$ to receive 3.2 g. A mixture of this precipitate (3.2 g) and sodium disulfite (10.4 g; 54.7 mmol) was well stirred in water (21 ml) at 60° C. using magnetic stirrer (with charcoal: 2 teaspoons). After cooling, the mixture was filtered and the precipitate washed with water. Concentrated HCl (35 ml) was added to the combined filtrate and washings, the solution was stirred with heating until the evolution gas $SO_2$ ceased, and then concentrated to get solid+solution (10 ml). After standing overnight the separated solid was filtered, dissolved in hot water (70 ml) and the solution was treated with charcoal and then filtered. Upon addition of $NaOAc.3H_2O$ (4.2 g) to the filtrate the free base separated, which was filtered and washed with water. Yield: 1.0 g. It was recrystallized from benzene to form almost colorless prisms. M.p. 177–8° C. (in capillary).

Example 8

Synthesis of 5-(2-methyl-2-nitropropyl)-8-hydroxyquinoline (9)

A solution of 2-nitropropane (30 ml, 0.33 mmol) in DMF (20 ml) was added to a mixture of 5-chloromethyl-8-hydroxy-quinoline hydrochloride (3 g; 13 mmol) and potassium tert-butoxide (5.6 g, 50 mmol) at 5° C. under Ar atmosphere. The reaction mixture was stirred for 24 h at room temperature. $CHCl_3$ (100 ml) was then added, and the solution was washed with water until a neutral pH was obtained. It was then washed with brine, dried over $Na_2SO_4$ and evaporated to dryness under vacuum (50° C./1 mm/Hg). The residue was crystallized from ethanol (50 ml) yielding 1.4 g (43%) of the title product. M.p. 133–134° C.; TLC $(CHCl_3/MeOH/NH_3$-8:2:0.5) $R_f$=0.8.

Example 9

Synthesis of 5-methoxymethyl-8-hydroxyquinoline (10)

5-Chloromethyl-8-hydroxyquinoline hydrochloride (2.145 g; 9.3 mmol) was added to a mixture of sodium methoxide (1.763 g; 32.6 mmol) in MeOH (40 ml). The reaction mixture was stirred for about 4 h at room temperature, and then evaporated to dryness. The residue was dissolved in $CHCl_3$ (100 ml, the solution was washed with water until a neutral pH was obtained, and was then washed with brine, dried over $Na_2SO_4$ and evaporated to dryness. The residue was extracted with hexane (100 ml). The hexane solution was evaporated to give the title product, 0.36 g (20%). M.p. 75–760° C. TLC ($CHCl_3$/MeOH/$NH_3$.9.5:0.5:0.1). $R_f$=0.36.

Example 10

Synthesis of 5-diethylaminomethyl-8-hydroxyquinoline (11)

Diethylamine (2.4 ml; 23.2 mmol) was added to a mixture of 5-chloromethyl-8-hydroxyquinoline hydrochloride (2.131 g; 9.25 mmol) in $CHCl_3$ (50 ml) at 5° C. The reaction mixture was stirred for 24 h at room temperature. $CHCl_3$ (50 ml) was then added and the solution was washed with 5% $NaHCO_3$ (2×50 ml) and brine (50 ml) and dried over $Na_2SO_4$. The solution was filtered and evaporated to dryness. The residue was crystallized from hexane (~10–15 ml) and gave 1.23 g (58%) of the product. An analytic sample of the title product was obtained by sublimation (80° C./1 mm Hg): M.p.=71–72° C.

Example 11

Synthesis of 5-piperidinomethyl-8-hydroxyquinoline (12)

Piperidine (2 ml; 20.26 mmol) was added to a solution of 5-chloromethyl-8-hydroxyquinoline (1.87 g; 8.13 mmol) in $CHCl_3$ (50 ml) at 5° C. The mixture was stirred for two days at room temperature. Then the mixture was evaporated under vacuum to dryness. The residue was dissolved in $CHCl_3$, washed with 5% $NaHCO_3$ (2×50 ml), followed by brine (50 ml), dried over $Na_2SO_4$ and evaporated to dryness. The residue was crystallized from hexane to give 1.0 g of the title product (50%). M.p. 96° C. TLC ($CHCl_3$; MeOH; $NH_3$=8:2:0.5). $R_f$=0.63.

Example 12

Synthesis of 5-morpholinomethyl-8-hydroxyquinoline (13)

Morpholine (1.9 ml; 21.8 mmol) was added to a solution of 5-chloromethyl-8-hydroxyquinoline (1.98 g; 8.34 mmol) in $CHCl_3$ (50 ml) at 5° C. The reaction mixture was stirred overnight at room temperature. Then $CHCl_3$ (100 ml) was added and the solution was washed with 5% $NaHCO_3$ (2×50 ml), followed by brine (50 ml), and dried over $Na_2SO_4$. The solution was filtered and evaporated under vacuum to dryness. The residue was crystallized from hexane-$CHCl_3$ and gave 1.2 g (59%) of the title product. M.p. 130° C. TLC ($CHCl_3$; MeOH; $NH_3$=8:2:0.5. $R_f$=0.69.

Example 13

Synthesis of 5-(4-methylpiperazinomethyl)-5-hydroxyquinoline (14)

N-methylpiperazine (5.0 ml), 45 mmol) was added to a mixture of 5-chloromethyl-8-hydroxyquinoline hydrochloride (4.1 g; 17.8 mmol) in $CHCl_3$ (80 ml) at 5° C. The mixture was stirred for 24 h at room temperature. $CHCl_3$ (100 ml) was then added and the solution was washed with 5% $NaHCO_3$ (3×50 ml) and brine 2×50 ml) and then dried over $Na_2SO_4$. The solution was filtered and evaporated to dryness. The residue was crystallized from a mixture of benzene-hexane and gave 2.89 g (63%) of the title product. M.p. 126–127° C. TLC ($CHCl_3$-MeOH-$NH_3$ 9:1:0.1) $R_f$=0.35.

Example 14

Synthesis of 5-(4-(2-hydroxyethyl)piperazin-1-ylmethyl)-8-hydroxyquinoline (15)

4-(2-Hydroxyethyl)-piperazine (7.2 ml; 58.7 mmol) was added to a suspension of 5-chloromethyl-8-hydroxyquinoline (5.413 g; 23.5 mmol) in $CHCl_3$ (80 ml) at 0° C. The mixture was stirred overnight at room temperature. The reaction mixture was subsequently washed with a saturated $NaHCO_3$ solution and brine, then dried with $Na_2SO_4$ and evaporated to dryness. Crystallization of the residue from a mixture of $CHCl_3$-Hex gave 4.05 g (60%) of title product. M.p. 123–4° C. The mother liquor was evaporated and the residue was crystallized to yield 1.5 g of title product. Overall yield: 5.55 g (82%). A highly pure product was obtained by soxleth extraction using hexane as the extractant. TLC ($CHCl_3$ MeOH $NH_3$=8:2:0.5). $R_f$=0.4.

Example 15

Synthesis of 5-(4-ethoxycarbonylpiperazinomethy)-8-hydroxyquinoline (16)

N-Ethoxycarbonylpiperazine (1.5 ml, 10.2 mmol) was added to a mixture of 5-chloromethyl-8-hydroxyquinoline hydrochloride (2.36 g, 10.2 mmol) and diisopropylethylamine (3.6 ml, 20.6 mmol) in $CHCl_3$ (50 ml) at 5° C. The mixture was stirred for 24 h at room temperature. $CHCl_3$ (100 ml) was then added and the solution was washed with 5% $NaHCO_3$ (3×50 ml) and brine (2×50 ml) and then dried over $Na_2SO_4$. The solution was filtered and evaporated to dryness. The residue was crystallized from a mixture of benzene hexane and gave 1.38 g (42%) of the title product. M.p. –96° C. TLC ($CHCl_3$-MeOH-$NH_3$ 9:1:0.1) $R_f$=0.6; TLC ($CHCl_3$-MeOH-$Me_3$ 9:0.5:0.05) $R_f$–0.4.

Example 16

Synthesis of 5-(imidazol-1-ylmethyl)-8-hydroxyquinoline (17)

A mixture of 5-chloromethyl-8-hydroxyquinoline hydrochloride (3.45 g; 15 mmol), imidazole (1.02 g; 15 mmol) and diisopropylethylamine (5.25 ml; 30 mmol) in $CHCl_3$ (60 ml) was stirred for 24 h at room temperature and then for 3 h at 60° C. After cooling, the mixture was evaporated, washed with ethyl acetate (50 ml) and then hexane (50 ml). The residue was crystallized from a mixture of toluene and ethanol (abs.) to give 0.83 g (29%) of title product. M.p. 182° C.

Example 17

Synthesis of N-Boc-Piperazine (18)

A solution of di-tertbutyl dicarbonate (0.217 g, 1 mmol) in absolute methanol was added dropwise to piperazine (0.172 g, 2 mmol) in absolute methanol (10 ml) during 0.5 h with stirring. The reaction mixture was stirred for 2 h, then the methanol was evaporated and the residue dissolved in ethylacetate (50 ml) The ethyl acetate solution was then washed with distilled water (3 times, 10 ml) followed by 10% citric acid (15 ml) and then evaporated under vacuum at 40° C. The product was obtained as a white solid (0.175 g, 94% yield), m.p.=40–42° C. TLC: $R_f$=0.61, $CH_3Cl:MeOH:NH_3$(aq) 9:1:0.25. $^1$H NMR-δ ($CDCl_3$)=1.42 (9H, s, $H_3$) Elemental analysis: $C_9H_{18}N_2O_2$ (M.W. 186.25)- Required: H-9.74; C-58.04; N-15.04. Found: H-9.62; C-58.15; N-14.93.

Example 18

Synthesis of 5-(N'-Boc-piperazinomethyl)-8-hydroxyquinoline (19)

5-Chloromethyl-8-hydroxyquinoline hydrochloride (1 g. 4.35 mmol), N-Boc-piperazine (Compound 18) (0.81 g, 4.35 mmol) and diisopropylethylamine (1.489 g, 2 ml, 11.5 mmol) were stirred in chloroform (30 ml) at room temperature overnight. Then chloroform (20 ml) was added and the reaction mixture washed with saturated sodium carbonate solution (15 ml×2) followed by brine (20 ml). The organic phase was separated and dried over anhydrous sodium sulfate overnight. Then the chloroform solution was evaporated under vacuum at room temperature. The product obtained was a green compound (1.36 g, 91%). Crystallization from benzene yielded green crystals, m.p.=118–120° C. TLC: $R_f$=0.61, $CH_3Cl:MeOH:NH_3$(aq) 9:1:0.25.

$^1$H NMR-δ ($CDCl_3$)=8.77 (1H, dd, J1=4.19 Hz, J2=1.54 Hz, $H_2$); 8.65 (1H, dd, J1=8.55 Hz, J2=1.57 Hz, $H_4$); 7.45 (1H, dd, J1=8.55 Hz, J2=4.20 Hz, $H_3$); 7.31 (1H, d, J=7.73 Hz, $H_6$); 7.06 (1H, d, J=7.72 Hz, $H_7$); 3.80 (2H, s, $H_5$); 3.37 (4H, s, $H_{10}$); 2.40 (4H, s, $H_9$); 1.43 (9H, s, $H_{11}$). Elemental analysis- $C_{19}B_{25}N_3O_3$ (M.W. 343.19). Required: H-7.34; C-66.44; N-12.24. Found: H-7.22; C-66.10; N-12.21.

Example 19

Synthesis of 5-piperazinomethyl-8-hydroxyquinoline trichloride (20)

Compound 19 (1 g) was dissolved in dry dioxane (30 ml) 4M HCl in dioxane (20 ml) was added and the reaction mixture was stirred for 2 h at room temperature. The dioxane was then removed under vacuum at 60° C. to obtain the product as a yellow powder (1.1 g, 100%).

Neutralization of the product: the product (0.150 g) was dissolved in $H_2O$ (25 ml). $NaHCO_3$ (sat) (25 ml) was added and the solution was stirred for 20 min. Then chloroform (150 ml) was added and the mixture stirred for a further 30 min. The two phases separated, the organic phase was dried over $Na_2SO_4$, filtered and evaporated. The white powder obtained was refluxed with benzene (50 ml) using a Din-Stark apparatus, followed by reflux with pentene (50 ml). After complete evaporation of pentene, the free base product was obtained as a white powder (0.76 g). m.p.=232–234° C. (with decomposition.) TLC: $R_f$=0.28, $CH_3Cl:MeOH:NH_3$ (aq) 9:1:0.25.

$^1$H NMR δ ($CDCl_3$)=8.77 (1H, dd, J1=4.18 Hz, J2=1.54 Hz, $H_2$); 8.66 (1H, dd, J1=8.53 Hz, J2=1.54 Hz, $H_4$); 7.45 (1H, dd, J1=8.55 Hz, J2=4.20 Hz, $H_3$); 7.31 (1H, d, J=7.73 Hz, $H_6$); 7.05 (1H, d, J=7.71 Hz, $H_7$); 3.77 (2H, s, $H_5$); 2.84 (4H, t, J=4.87 Hz, $H_{10}$); 2.44 (4H, not resolved triplet, $N_9$). Elemental analysis-$C_{14}H_{17}N_3O$ (M.W. 243.13). Required: H-7.00; C-69.14. Found: H-6.89; C-67.97.

Example 20

Synthesis of N,N'-di-(8-hydroxyquinolin-5-ylmethyl)-piperazine tetrachloride (21)

5-Chloromethyl-8-hydroxyquinoline hydrochloride (1.5 g, 3 equivalents) was added to absolute chloroform (40 ml) followed by the addition of diisopropylethylamine (2.27 ml, 6 equivalents) at 5° C. The reaction mixture was shaked it became clear, then piperazine (0.187 g, 1 equivalent) was added and the reaction mixture was shaked 36 h. The white precipitate was filtered and dissolved in 2M hydrochloric acid (40 ml) Yellow water solution was then liofilized to get 1 g (84%) of yellow powder.

For the elemental analysis, NMR, and melting point measurements hydrochloric acid-free (neutral) compound was prepared. Bis-hydroxyquinoline tetrachloride (200 mg) was dissolved in water (25 ml), and then saturated sodium hydrocarbonate solution (25 ml) was added and the mixture was shaked for 20 minutes. Then chloroform (150 ml) was added. Water-chloroform mixture was shaked strongly 30 minutes and then chloroform solution was separated from water, dried overnight with anhydrous sodium sulphate and then evaporated. White powder was then boiled with benzene (50 ml) using Din-Stark attachment, and then boiled with pentene (50 ml) After the complete evaporation of pentene, 93 mg of white powder was obtained, m.p=227–228° C. TLC: $R_f$=0.27, $CH_3Cl:MeOH:NH_3$(aq) 9:1:0.25.

$^1$H NMR δ ($CDCl_3$)=8.76 (2H, dd, J1=4.20 Hz, J2=1.52 Hz, 2×$H_2$); 8.64 (2H, dd, J1=8.52 Hz, J2=1.28 Hz, 2×$H_4$); 7.45 (2H, dd, J1=8.52 Hz, J2=4.20 Hz, 2×$H_3$); 7.31 (2H, d, J=7.68 Hz, 2×$H_6$); 7.05 (2H, d, J=7.72 Hz, 2×$H_7$); 3.80 (4H, s, 4×$H_5$); 2.49 (8H, not resolved, 8×$H_9$) Elemental analysis-$C_{24}H_{24}N_4O_2$ (M.W. 400.48). Required: H-6.00; C-72.00. Found: H-6.18; C-71.88.

Example 21

Synthesis of N-Formylpiperazine (22)

Methylformiate (20 ml, 290 mmol) was added at 5° C. to piperazine (25 g, 290 mmol) and the reaction mixture was stirred 2 h at room temperature, followed by 12 h at 80° C. (in an oil bath while the flask was equiped with a reflux condenser). Methanol was removed under vacuum at 50° C. and then piperazine was removed by sublimation at vacuum at 100° C. (The reaction mixture was heated until condensation of piperazine was finished.) The product was obtained as colourless liquid that was condensed at ~130° C. (yield: 18 ml (61%), $n_{20}^d$=1.121 g/l. TLC: $R_f$=0.45, $CH_3C_1:MeOH:NH_3$(aq) 9:1:0.25.

$^1$H NMR-δ ($CDCl_3$)=7.99 (1H, s, $H_4$) Elemental analysis-$C_5H_6N_2O$ (M.W. 110.12). Required: H-5.49; C-54.54; N-25.44. Found: H-5.71; C-54.23; N-25.11.

Example 22

Synthesis of 5-(4-formylpiperazinomethyl)-8-hydroxyquinoline (23)

5-Chloromethyl-8-hydroxyquinoline hydrochloride (2.26 g, 9.8 mmol) piperazine formamide (1.0 g, 9 mmol) and diisopropylethylamine (2.75 g, 21 mmol) were stirred in chloroform (30 ml) for 48 h. Then chloroform (150 ml) was added and the reaction mixture was washed with $Na_2CO_3$ (25 ml×2), followed by brine (20 ml). The organic phase was dried over $Na_2SO_4$ for 8 h, filtered and evaporated. The product was obtained as a green solid (2.2 g, 95%) which was crystallized from benzene. m.p.=172–174° C. Additional purification of the product could be done by crystallization from benzene. TLC: $R_f$=0.49, $CH_3Cl:MeOH:NH_3$ (aq) 9:1:0.25.

$^1$H NMR δ ($CDCl_3$)=8.78 (1H, dd, J1=4.20 Hz, J2=1.56 Hz, $H_2$); 8.62 (1H, dd, J1=8.55 Hz, J2=1.57 Hz, $H_4$); 8.00

(1H, s, $H_{11}$); 7.46 (1H, dd, J1=8.54 Hz, J2=4.19 Hz, $H_3$); 7.31 (1H, d, J=7.73 Hz, $H_6$); 7.06 (1H, d, J=7.71 Hz, $H_7$); 3.82 (2H, s, 2×$H_5$). Elemental analysis-$C_{14}H_{17}N_3O$ (M.W. 243.31). Required: H-6.27; C-66.34; N-15.48. Found: H-6.31; C-66.11; N-15.41.

Example 23

Synthesis of 5-piperazinomethyl-8-hydroxyquinoline trichloride (20) (Alternative Method)

A solution of ~16% HCl in methanol (25 ml) was added to a solution of compound 23 (300 ng, 1.23 mmol) in absolute methanol (5 ml). (Upon addition of the acid, all insoluble material was dissolved). The reaction mixture was stirred at room temperature. After 10 min, a yellow powder was precipitated; the mixture was stirred overnight. The product was then filtered and washed with absolute methanol (5 ml×2). The product was obtained as a yellow powder in quantitative yield. TLC and the m.p. showed the product to be identical to that obtained previously.

Example 24

Synthesis of 5-cyanomethyl-8-hydroxyquinoline (24)

5-Chloromethyl-8-hydroxyquinoline hydrochloride (2.5 g, 1 mmol) was dissolved in DMSO (15 ml, technical grade). The solution was cooled in an ice bath and diisopropylethylamine (3 ml, 16.7 mmol) was added. The mixture was stirred until all starting material had dissolved. Subsequently, a solution of NaCN (2 g, 40 mmol) in DMSO (10 ml, technical grade) was prepared in a 50 ml flask and cooled in an ice bath. The hydroxyquinoline was then added dropwise during ~6 minutes. The ice bath was then removed and the reaction mixture was stirred for 3.5 h at 45° C. The mixture was then added to an ice-cold solution of $NaHCO_3$ (sat) (50 ml) and $H_2O$ (50 ml). The product precipitated during ~20 min. The mixture was then filtered and the solid was washed twice with cold water (20 ml+30 ml), and dried under high vacuum to remove traces of water. The product was obtained as a white powder (1.06 g, 53%), m.p.=171–172° C. TLC: $R_f$=0.43, $CH_3C_1$:MeOH:$NH_3$(aq) 9:1:0.25.

$^1$H NMR δ ($CDCl_3$)=8.77 (1H, dd, $J_1$=4.19 Hz, $J_2$=1.54 Hz, $H_2$); 8.65 (1H, dd, $J_1$=8.55 Hz, $J_2$=1.57 Hz, $H_4$); 7.45 (1H, dd, $J_1$=8.55 Hz, $J_2$=4.20 Hz, $H_3$); 7.31 (1H, d, J=7.73 Hz, $H_6$); 7.06 (1H, d, J=7.72 Hz, $H_7$); 3.80 (2H, s, $H_5$); Elemental analysis-$C_{11}H_9N_2O$ (M.W. 184.20). Required: H-4.34; C-71.66; N-15.20. Found: H-4.33; C-71.93; N-14.89.

Example 25

Synthesis of N,N'-di-(8-hydroxyquinolin-5-y1-methyl)-homopiperazine (25)

5-Chloromethyl-8-hydroxyquinoline hydrochloride (1.5 g, 6.5 mmol) was dissolved in abs $CHCl_3$ (40 ml). Diisopropylethylamine (2.82 g, 22 mmol) was added. The mixture was stirred until all material had dissolved. Homopiperazine (0.2 g, 2 mmol) was then added, and the mixture stirred for a further 48 h at room temperature. Subsequently, $CHCl_3$ (200 ml) was added and the mixture was washed with $NaHCO_3$(sat) and then with water. The organic phase was dried overnight over $Na_2SO_4$, filtered and the solvent evaporated to yield a white powder (0.75 g). The dry product was obtained by azeotropic distillation with benzene, followed by reflux with pentene and evaporation, yielding a white powder (0.7 g, 65%). m.p=155–157° C. TLC: $R_f$=0.32, $CH_3Cl$:MeOH:$NH_3$(aq) 9:1:0.25.

$^1$H NMR δ ($CDCl_3$)=8.76 (2H, dd, $J_1$=4.16 Hz, $J_2$=1.53 Hz, 2×$H_2$); 8.68 (2H, dd, $J_1$=8.53 Hz, $J_2$=1.45 Hz, 2×$H_4$); 7.43 (2H, dd, J=8.54 Hz, $J_2$=4.21 Hz, 2×$H_3$); 7.25 (2H, d, J=3.49 Hz, 2×$H_6$); 7.03 (2H, d, J=7.71 Hz, 2×$H_7$); 3.88 (4H, s, 4×$H_5$); 2.72 (4H, t, J=5.89, 4×$H_9$); 2.61 (4H, s, 4×$H_{11}$); 1.75 (2H, t, J=5.56, 2×$H_{10}$). Elemental analysis-$C_{25}H_{26}N_4O_2$ (M.W. 414.51). Required: H-6.28; C-72.46; N-13.53. Found: H-6.10; C-73.13; N-12.97.

Example 26

Synthesis of 5-thiomorpholinomethyl-8-hydroxyquinoline (26)

Thiomorpholine (1 ml; 10 mM) was added to a solution of 5-chloromethyl-8-quinolinol hydrochloride (2.3 g; 10 mM) and DIEA (3.5 ml; 20.1 mM) in chloroform (50 ml) at 5° C. The reaction mixture was stirred for 24 h at room temperature. 50 ml of chloroform was then added and the solution was washed twice with 50 ml of 5% sodium hydrocarbonate solution. Then the chloroform solution was filtered and evaporated to dryness. The residue was then crystallized from hexane-$CHCl_2$ and gave 1.5 g (58%) of the product, m.p.=121–122° C. TLC: $R_f$=0.39, $CH_3Cl$:MeOH:$NH_3$(aq) 9:1:0.25.

$^1$H NMR δ ($CDCl_3$)=8.78 (1H, dd, J1=4.17 Hz, J2=1.56 Hz, H2); 8.64 (1H, dd, J1=8.52 Hz, J2=1.55 Hz, H4); 7.45 (1H, dd, J1=8.56 Hz, J2=4.21 Hz, H3); 7.31 (1H, d, J=7.73 Hz, H6); 7.07 (1H, d, J=7.72 Hz, H7); 3.80 (1H, s, H5). Elemental analysis-$C_{14}H_{16}N_2S$ (M.W. 260.35). Required: N-10.76; S-12.31. Found: N-10.59; S-12.19.

Example 27

Prevention of Lipid Peroxidation in Brain Tissue

Brain cortex homogenates (10% wt/vol) from male Wistar rats were prepared in 0.3M sucrose and incubated in air as described (Rehncrona et al., (1980) J. Neurochem. 34: 1630–38). Aliquots (0.1 ml) of homogenate were incubated alone at 30° C. for 90 min to determine basal lipid peroxidation, or incubated after the addition of $10^{-4}$ $Fe_2$ ($SO_4$), or $FeCl_3$ and in the presence of $10^{-3}$M iron chelator of formula I or II. For the assay, to 0.3 ml of the homogenate there were added 0.2 ml of 8% SDS, 1.5 ml of 20% acetic acid pH 3.0–3.5, 1.5 ml of 0.8% thiobarbituric acid (TBA) and 0.5 ml of $H_2O_2$×2, the mixture was incubated at 95° C. for 60 min, cooled and lipid peroxidation was assayed by measurement of malondialdehyde formation at 532 nm, as described (Dexter et al. (1989) J. Neurobiochem. 52: 381–89). Standard curve: 1,1,3,3-tetraethoxypropane 0.1–25 nmol in 0.3 ml.

The Compounds 1, 3 and 15 reduced iron-induced MDA formation by 50% approximately, at a concentration of $10^{-3}$M for each chelator and of $10^{-4}$M for ferric chloride.

In another experiment, the Compounds 3, 7, 9–17 and 26 were examined for their ability to inhibit lipid peroxidation in vitro by measuring their capability to inhibit MDA formation in the presence of $10^{-4}$M $FeCl_3$ in rat brain homogenates. Ferric chloride($10^{-4}$M)-induced lipid peroxidation, as measured by MDA formation in rat cerebral cortex homogenates, was inhibited to a different degree by $10^{-3}$M of the various chelators. All compounds tested inhibited MDA formation, but the Compounds 3, 11–16 and 26 were found to be more effective.

It is important to note that the in vitro results may not parallel the in vivo anti-oxidant potentials of the chelators but give only an indication of their ability to reduce oxidative stress. Anti-oxidant activity of any drug in vivo may be affected by many parameters, e.g. the ability to cross membranes, the interaction with surrounding molecules, the local pH and ionic strength etc.

Example 28

Prevention of 6-OHDA-induced Toxicity in Rats

Out of the iron chelators examined in vitro in Example 27, two different types of iron chelators, namely Compound 3 and Compound 15, which were most effective in inhibiting MDA formation, were chosen for in vivo studies, in which the chelators (200 μg) were injected intraventricularly in rats alone or prior to 6-OHDA (250 μg).

Male Sprague-Dawley rats, weighing 230–270 g, were housed in a controlled-temperature room with a standardized dark-light schedule (12/12 h) for 4 weeks. Rats were anesthetized with a mixture of 15 mg/kg of pentobarbital and 60 mg/kg of chloral hydrate. 6-OHDA (250 μg in 5 μl of 0.9% NaCl containing 0.2% ascorbic acid), the chelator 3 or 15 (200 μg in 5 μl), a combination of both (the chelator 3 or 15 15 min before 6-OHDA), or saline (5 μl) (control) was injected into the right cerebral ventricle using stereotactic techniques. The coordinates with bregma as the reference were D 0.8 mm, L 1.3 mm, and V 3.6 mm according to the atlas of Paxinos and Watson. Pargyline (50 mg/kg i.p.) and desmethylimipramine-HCl (25 mg/kg i.p.) were administered to all the rats 60 min before intracerebroventricular injection. Pargyline inhibits monoamine oxidase and thereby enhances the toxicity of 6-OHDA, and desmethylimipramine provides protection for central noradrenergic neurons from the toxin. All the animals received a daily injection of isotonic glucose (4 ml/day i.p.) until they regained their original body weight. Behavioral tests were performed 4 weeks after operation, commencing between 8 and 10 a.m. The rats were killed after the behavioral studies. Desferal was obtained from Ciba Geigy, and other chemicals were from Sigma (St. Louis, Mo., U.S.A.).

For behavioral studies, rats were placed on a Varimax activity meter (Columbus Instruments). Horizontal spontaneous locomotor activity in a novel space was measured during the first 5 min. Rearing activity (spontaneous lifting of the two front paws off the cage floor) was determined every fourth minute for 30 min by direct observation by two individuals blind to the treatment.

Norepinephrine (NE), DA, and metabolite levels were measured as follows: four weeks postoperatively, rats were killed by decapitation, and the brains were rapidly removed. The striata were dissected on an ice-chilled glass plate and quickly frozen in liquid nitrogen. The endogenous levels of NE, DA, 3,4-dihydroxyphenylacetic acid (DOPAC), and homovanillic acid (HVA) were determined by HPLC with electrochemical detection (Ben-Shachar et al. (1991) Eur. J. Pharmacol. 202:177–83). All data are expressed as mean±SEM values. Statistical analysis was carried out by analysis of variance with multiple comparisons followed by Student's t test.

Striatal dopamine and its metabolites DOPAC and HVA concentrations, which were determined by HPLC, served as a criteria for the extent of the damage caused by 6-OHDA in the presence or absence of the iron chelators. The specificity of the effects of 6-OHDA and of the chelators 3 and 5 was established by studying the changes in striatal norepinephrine (NE) and serotonine (5-HT) and its main metabolite 5-HIAA (5-hydroxy-indole acetic acid) Both Compounds 3 and 15 at a dose of 200 μg efficiently prevented the 6-OHDA-induced reduction in striatal dopamine and DOPAC concentrations in the rat The significant damage caused by 6-OHDA to the nigrostriatal dopamine neurons manifests itself in the increased dopamine turnover which is calculated by the ratio (DOPAC+HVA)/DA. Dopamine turnover was normal in rats pretreated with iron chelators (Table 1).

TABLE 1

Biogenic amines and their metabolites in the rat striatum after intraventricular injection of 200 μg of chelator 3 or 15 prior to 250 μg 6-OHDA

| pmol/mg tissue | saline (9) | 6-OHDA (9) | 15 Comb. (8) | 3 Comb. (8) |
|---|---|---|---|---|
| NE | 4.1 ± 0.2 | 5.0 ± 0.1 | 5.01 ± 0.1 | 4.7 ± 0.5 |
| DA | 47.4 ± 2.2 | 19.93 ± 5.0$^c$ | 33.8 ± 4.3 | 31.84 ± 5.3 |
| DOPAC | 2.31 ± 0.06 | 1.79 ± 0.25$^a$ | 2.45 ± 0.25 | 2.15 ± 0.28 |
| HVA | 1.96 ± 0.08 | 2.24 ± 0.23 | 2.67 ± 0.33 | 2.68 ± 0.43 |
| 5-HT | 4.50 ± 0.51 | 4.00 ± 0.35 | 4.24 ± 0.43 | 4.40 ± 0.41 |
| 5-HIAA | 4.10 ± 0.29 | 3.76 ± 0.20 | 4.48 ± 0.38 | 4.60 ± 0.53 |
| (DOPAC + HAV)/DA | 0.09 | 0.202 | 0.15 | 0.15 |

Number in brackets represents the number of animals in each treatment.
Comb. stands for 200 μg chelators + 250 μg 6-OHDA.
$^a$-$p < 0.05$,
$^b$-$p < 0.025$,
$^c$-$p < 0.001$.

Based on confirmation properties of the two iron chelators 3 and 15, it was considered that Compound 15 has a better chance to cross the blood-brain-barrier (BBB) and the studies were continued with Compound 15. In order to decrease to minimum the possibility of a direct interaction between the chelator and the toxin as a cause for the protection, and to try to find a smaller effective dose of the chelator, 1 μg Compound 15 was injected intraventricularly prior to the injection of 250 μg 6-OHDA. Table 2 shows that even at this dose Compound 15 was effective in preventing 6-OHDA-induced lesion.

TABLE 2

Biogenic amines and their metabolites in the rat striatum after intraventricular injection of 1 μg of chelator 15 prior to 250 μg 6-OHDA.

| pmol/mg tissue | saline (8) | 6-OHDA (7) | 15 Comb. (8) |
|---|---|---|---|
| NE | 1.4 ± 0.1 | 1.1 ± 0.1 | 1.3 ± 0.12 |
| DA | 5.29 ± 6.4 | 12.93 ± 3.3$^a$ | 62.9 ± 3.13 |
| DOPAC | 2.81 ± 0.5 | 0.76 ± 0.11$^a$ | 2.49 ± 0.13 |
| HVA | 2.67 ± 0.18 | 1.10 ± 0.21$^a$ | 2.77 ± 0.25 |
| 5-HT | 3.33 ± 0.53 | 3.22 ± 0.42 | 4.84 ± 0.45 |
| 5-HIAA | 5.29 ± 0.53 | 6.29 ± 0.65 | 4.98 ± 0.46 |
| (DOPAC + HAV)/DA | 0.09 | 0.14 | 0.08 |

Number in brackets represents the number of animals in each treatment.
Comb. stand for 1 μg chelator 15 + 250 μg 6-OHDA.
$^a$-$p < 0.001$.

The main goal at this stage of research was to find out whether Compound 15 given peripherally would be able to prevent 6-OHDA-induced toxicity. In other words the question was whether the chelator will stay stable in the periphery, cross the BBB and Compound 15 (5 mg/Kg i.p) for 10 days. Control group received phosphate buffer pH–6.4 0.1M. On the 11$^{th}$ day, the rats of both groups were injected intraventricularly with 250 μg 6-OHDA. Partial but significant protection against 6-OHDA toxicity was observed with peripheral pretreatment with Compound 15 (Table 3).

As expected, the neurotoxin 6-OHDA caused an 80% decrease in striatal dopamine levels which was accompanied by a significant decrease in its metabolites DOPAC and HVA. Intraperitoneal treatment with Compound 15 for 10 days before intraventricular injection of 6-OHDA (combination) partially protected the dopaminergic neurons from degeneration as expressed by dopamine, DOPAC and HVA levels (not shown).

TABLE 3

Biogenic amines and their metabolites in the rat striatum after chronic peripheral injection of 5 mg/Kg Compound 15 prior to intraventricular injection of 250 μg 6-OHDA

| pmol/mg tissue | saline (6) | 6_OHDA (7) | 15 Comb. (8) |
|---|---|---|---|
| NE | 1.09 ± 0.03 | 1.22 ± 0.04 | 1.21 ± 0.4 |
| DA | 49.2 ± 2.59 | 9.69 ± 2.63[a] | 24.4 ± 4.4[ab] |
| DOPAC | 2.02 ± 0.28 | 0.51 ± 0.11[A] | 1.4 ± 0.25 |
| HVA | 2.56 ± 0.22 | 1.05 ± 0.19[A] | 2.28 ± 0.75 |
| 5-HT | 2.99 ± 0.18 | 2.60 ± 0.15 | 2.6 ± 0.31 |
| 5-HIAA | 1.53 ± 0.09 | 1.57 ± 0.07 | 1.59 ± 0.16 |
| (DOPAC + HAV)/DA | 0.09 | 0.16 | 0.15 |

Number in brackets represents the number of animals in each treatment.
Comb. stand for chelator 15 (5 mg/Kg/day i.p. for 10 days) + 250 μg 6-OHDA.
[a]-$p < 0.001$ vs. saline;
[b]-$p < 0.01$ vs. 6-OHDA.

Appendix A

Structures of compounds I, II and 1-26

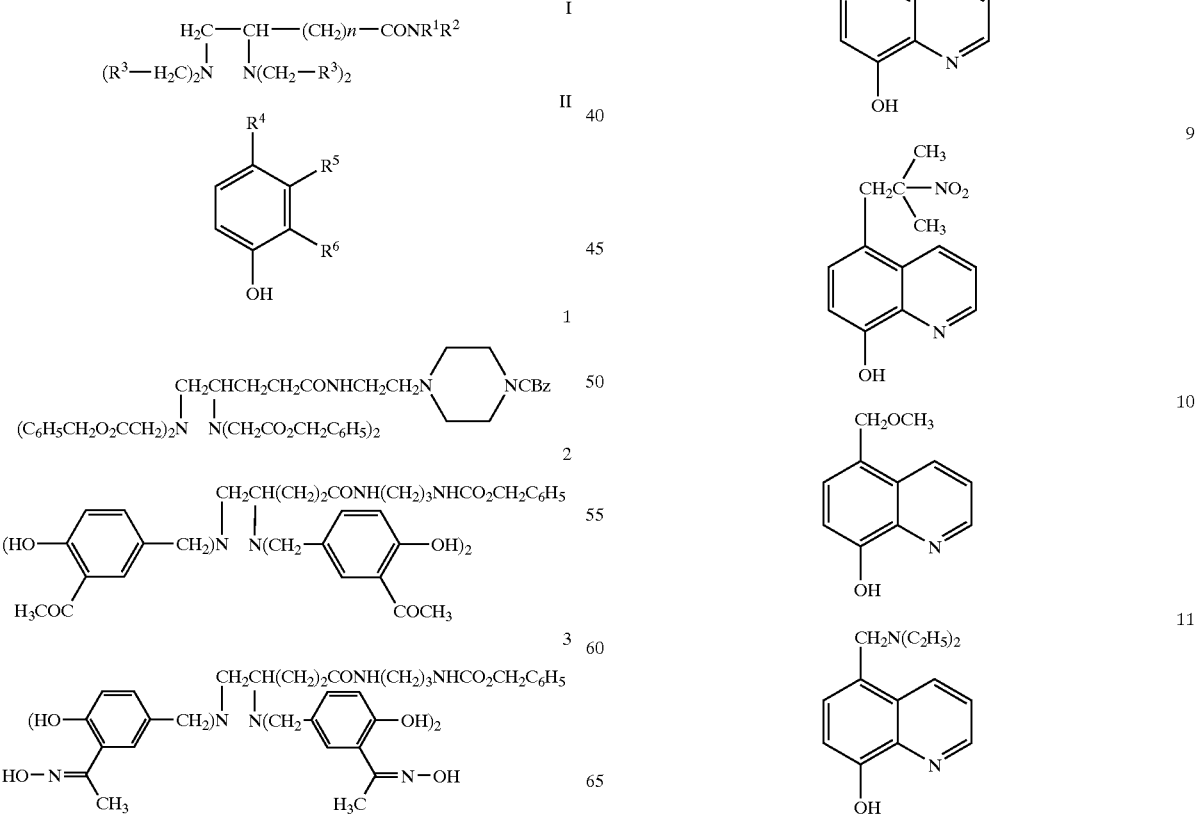

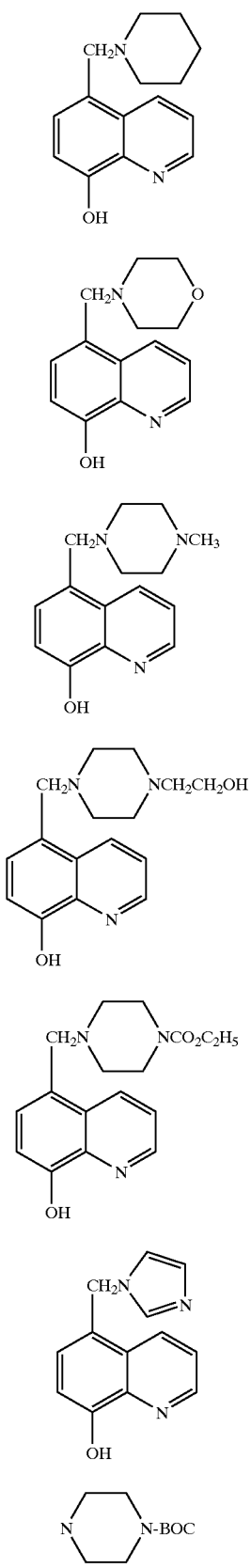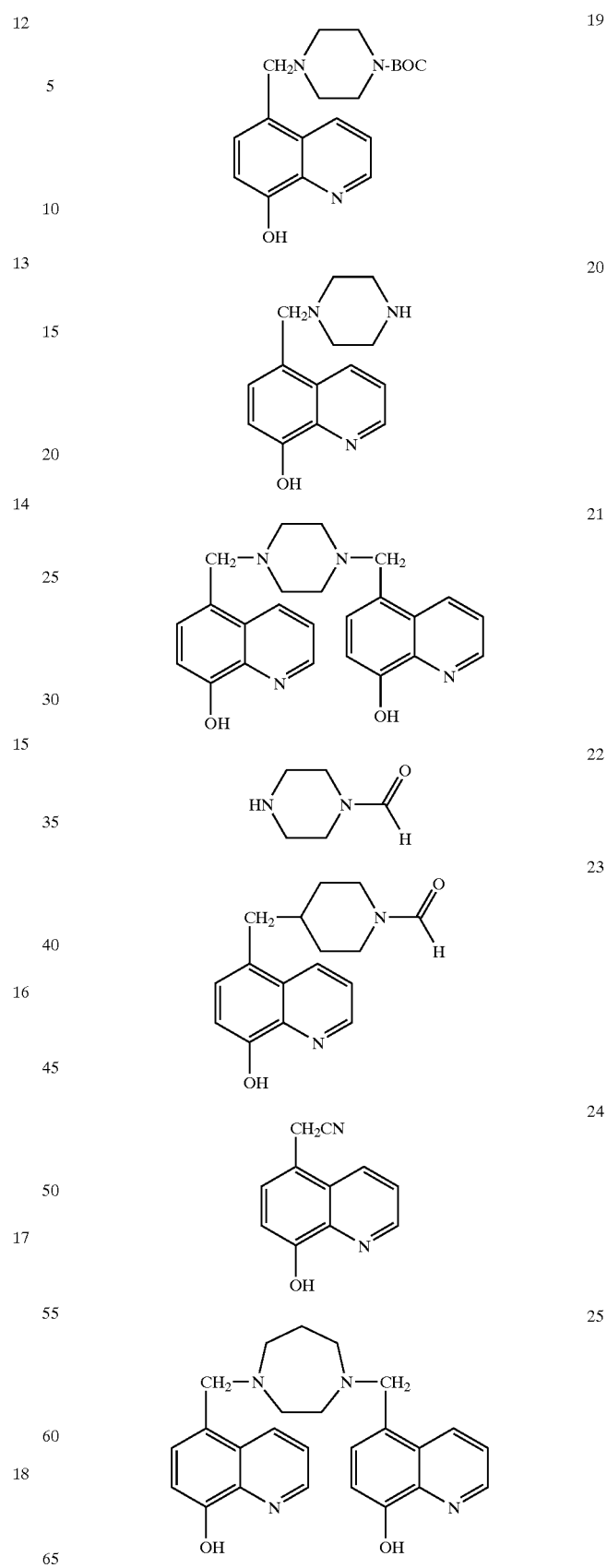

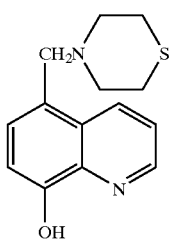

What is claimed is:

1. A method for prevention of lipid peroxidation in the brain which comprises administering to an individual in need thereof an effective amount of a compound selected from the group consisting of:

(a) a compound of formula I:

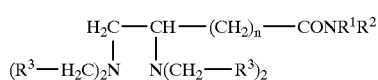

wherein $R^1$ is H or hydrocarbyl; $R^2$ is a hydrophobic radical; $R^3$ is a radical selected from the group consisting of 3-($C_2$-$C_6$)acyl-4-hydroxyphenyl, 3-hydroxyimino($C_2$-$C_6$) alkyl-4-hydroxyphenyl, and COOZ, wherein Z is H, ($C_1$-$C_6$)alkyl, aryl or ar($C_1$-$C_6$)alkyl; and n is an integer from 1 to 20; and (b) a compound of formula II:

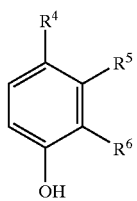

wherein $R^4$ is ($C_1$-$C_6$)acyl, nitro($C_1$-$C_6$)alkyl, cyano($C_1$-$C_6$) alkyl, ($C_1$-$C_6$)alkoxy($C_1$-$C_6$)alkyl or —$CH_2NR^7R^8$, wherein $R^7$ and $R^8$, the same or different, is each H or ($C_1$-$C_6$)alkyl, or together with the N atom form a saturated or unsaturated 5–7 membered ring optionally containing a further heteroatom selected from the group consisting of N, O and S, the further N atom in such saturated 5–7 membered ring being optionally substituted by ($C_1$-$C_6$)-alkyl, ($C_1$-$C_6$)-acyl, hydroxy-($C_1$-$C_6$)alkyl, ($C_1$-$C_6$)alkoxycarbonyl, and 8-hydroxyquinolin-5-yl-($C_1$-$C_6$)alkyl, and either $R^5$ is H and $R^6$ is ($C_2$-$C_6$)-acyl or hydroxyimino ($C_2$-$C_6$)alkyl, or $R^5$ and $R^6$ together with the phenyl ring form a quinoline, a 1,2,3,4-tetrahydroquinoline or a perhydroquinoline ring structure, or a pharmaceutically acceptable salt of a compound of formula I or II.

2. A method according to claim 1, wherein said compound is a compound of formula I wherein n is 2 to 4; $R^1$ is H or a saturated, unsaturated or aromatic hydrocarbyl radical; $R^2$ is a hydrophobic radical selected from the group consisting of ($C_6$-$C_{20}$)-alkyl, ($C_6$-$C_{20}$)-alkenyl, a radical selected from the group consisting of ($C_5$-$C_{20}$)-acyl, benzyloxycarbonyl, substituted benzyloxycarbonyl, ($C_3$-$C_8$)-alkoxycarbonyl, cycloalkoxycarbonyl and aryloxycarbonyl, said radical being either linked directly to the N atom or through a ($C_1$-$C_5$)-alkylene chain, and N-substituted amino or 4-substituted-piperazin-1-yl linked to the N atom through a ($C_1$-$C_5$)-alkylene chain; and $R^3$ is a radical selected from the group consisting of 3-($C_2$-$C_6$)acyl-4-hydroxyphenyl, 3-hydroxyimino($C_2$-$C_6$)alkyl-4-hydroxyphenyl, and COOZ, wherein Z is H, ($C_1$-$C_6$)alkyl, aryl or ar($C_1$-$C_6$) alkyl.

3. A method according to claim 2, wherein $R^2$ is straight or branched ($C_6$-$C_{20}$)-alkyl or alkenyl; saturated or unsaturated ($C_5$-$C_{20}$)-carboxylic acyl linked directly to the N atom or through a ($C_1$-$C_5$)-alkylene chain; benzyloxycarbonyl or halo-substituted benzyloxycarbonyl, linked directly to the N atom or through a ($C_1$-$C_5$)-alkylene chain; a bulky alkoxycarbonyl group, linked directly to the N atom or through a ($C_1$-$C_5$)-alkylene chain; cycloalkoxycarbonyl linked directly to the N atom or through a ($C_1$-$C_5$)-alkylene chain; aryloxycarbonyl, linked directly to the N atom or through a ($C_1$-$C_5$)-alkylene chain; or 4-substituted-piperazin-1-yl or N-substituted amino, linked to the N atom through a ($C_1$-$C_5$)-alkylene chain, wherein the 4- and N-substituent is a hydrophobic group selected from the group consisting of ($C_6$-$C_{20}$)-alkyl, ($C_6$-$C_{20}$)-alkenyl, ($C_5$-$C_{20}$)-acyl, benzyloxycarbonyl, substituted benzyloxycarbonyl, ($C_3$-$C_8$)-alkoxycarbonyl, cycloalkoxycarbonyl, aryloxycarbonyl, N-substituted amino and 4-substituted-piperazin-1-yl, all such substituents being as defined above.

4. A method according to claim 3, wherein n is 2, $R^1$ is H, $R^2$ is the radical —$(CH_2)_3NHCOOCH_2C_6H_5$, 5-(tert-butoxycarbonyl) pentyl, or —$(CH_2)_2$-(4-carbobenzoxy)-piperazin-1-yl, and $R^3$ is benzyloxycarbonyl, 3-(1-hydroxy-iminoethyl)-4-hydroxyphenyl or 3-acetyl-4-hydroxyphenyl.

5. A method according to claim 4, wherein said compound of formula I is selected from the group of compounds consisting of:

N-[2-(4-carbobenzoxypiperazin-1-yl)ethyl]-4,5-bis[bis (benzyloxycarbonylmethyl)amino]valeramide;

N-(3-benzyloxycarbonylaminopropyl)-4,5-bis[bis(3-acetyl-4-hydroxybenzyl)amino]valeramide;

N-(3-benzyloxycarbonylaminopropyl)-4,5-bis[bis(3-(1-hydroxy-iminoethyl)-4-hydroxybenzyl)amino] valeramide; and N-[5-(tert-butyloxycarbonyl)pentyl]-4,5-bis[(bis (benzyloxycarbonyl)methyl]amino]valeramide.

6. A method according to claim 1, wherein said compound is a compound of formula II wherein $R^4$ is ($C_1$-$C_6$)-acyl, nitro($C_1$-$C_6$)alkyl in which the ($C_1$-$C_6$)alkyl group may be branched, cyano($C_1$-$C_6$)alkyl, ($C_1$-$C_6$)-alkoxy($C_1$-$C_6$) alkyl, or $CH_2NR^7R^8$, in which $R^7$ and $R^8$ are both H, or one is H and the other is ($C_1$-$C_6$)-alkyl, or both $R^7$ and $R^8$ are ($C_1$-$C_6$)alkyl, or $R^7$ and $R^8$ together with the N-atom form a saturated or unsaturated 5–7 membered ring optionally containing a further heteroatom selected from the group consisting of N, O and S, the further N-atom in such saturated 5–7 membered ring being optionally substituted by ($C_1$-$C_6$)-alkyl, ($C_1$-$C_6$)-acyl, hydroxy-($C_1$-$C_6$)alkyl, ($C_1$-$C_6$)-alkoxycarbonyl, or 8-hydroxyquinolin-5-yl ($C_1$-$C_6$)alkyl.

7. A method according to claim 6, wherein $R^4$ is a radical selected from the group consisting of formyl, 2-methyl-2-nitropropyl, cyanomethyl, methoxymethyl, (diethyl)amino-methyl, piperidin-1ylmethyl, morpholin-1- ylmethyl, thiomorpholin-1-ylmethyl, piperazin-1-ylmethyl, imidazolylmethyl, 4-methyl-piperazin-1ylmethyl, 4-(2- hydroxyethyl)piperazin-1-ylmethyl, 4-formylpiperazin-1-ylmethyl, 4-(ethoxycarbonyl)piperazin-1ylmethyl, 4-(butoxycarbonyl)piperazin-1-ylmethyl, 4-(8-hydroxyquinolin-5-ylmethyl)-piperazin-1-ylmethyl, and 4-(8-hydroxy-quinolin-5-ylmethyl)homopiperazin-1-ylmethyl.

8. A method according to claim 6 or 7, wherein, in said compound of formula II, $R^5$ is H and $R^6$ is ($C_2$–$C_6$)-acyl or hydroxyimino($C_2$–$C_6$)alkyl.

9. A method according to claim 8, wherein said compound of formula II is selected from the group of compounds consisting of:
2-acetyl-4-[4-(2-hydroxyethyl)piperazin-1-yl-methyl]phenol; and
2-(1-hydroxyiminoethyl)-4-[4-(2-hydroxyethyl)piperazin-1-ylmethyl]phenol.

10. A method according to claim 6 or 7, wherein, in said compound of formula II, $R^5$ and $R^6$ together with the phenyl ring form a quinoline ring structure.

11. A method according to claim 10, wherein said quinoline compound is selected from the group consisting of:
5-formyl-8-hydroxyquinoline;
5-(2-methyl-2-nitropropyl)-8-hydroxyquinoline;
5-methoxymethyl-8-hydroxyquinoline;
5-diethylaminomethyl-8-hydroxyquinoline;
5-piperidinomethyl-8-hydroxyquinoline;
5-morpholinomethyl-8-hydroxyquinoline;
5-(4-methylpiperazin-1-ylmethyl)-8-hydroxyquinoline;
5-[4-(2-hydroxyethyl)piperazin-1-ylmethyl]-8-hydroxyquinoline;
5-[4-ethoxycarbonylpiperazin-1ylmethyl)-8-hydroxyquinoline;
5-(imidazol-1-ylmethyl)-8-hydroxyquinolin;
5-(4-Boc-piperazin-1-ylmethyl)-8-hydroxyquinoline;
5-piperazin-1-ylmethyl-8-hydroxyquinoline;
N,N'-di-(8-hydroxyquinolin-5-ylmethyl)piperazine;
5-(4-formylpiperazin-1-ylmethyl)-8-hydroxyquinoline;
5-cyanomethyl-8-hydroxyquinoline;
N,N'-di-(8-hydroxyquinolin-5-ylmethyl)homopiperazine; and
5-thiomorpholin-1-ylmethyl-8-hydroxyquinoline.

12. A method according to claim 1 for the treatment of a neurodegenerative disorder.

13. A method according to claim 12 wherein said neurodegenerative disorder is Parkinson's disease.

14. A method according to claim 1 for the treatment of stroke.

15. A method according to claim 11, which comprises administering to an individual in need thereof an effective amount of the compound 5-[4-(2-hydroxyethyl)piperazin-1-ylmethyl]-8-hydroxyquinoline.

16. A method according to claim 15 for the treatment of stroke.

17. A method according to claim 15 for the treatment of a neurodegenerative disorder.

18. A method according to claim 17 wherein said neurodegenerative disorder is Parkinson's disease.

19. A method for retarding dopaminergic neuron degeneration in the substantia nigra of the brain which comprises administering to an individual in need thereof an effective amount of the compound 5-[4-(2-hydroxyethyl)piperazin-1-ylmethyl]-8-hydroxyquinoline.

20. A method according to claim 19 for the treatment of neurodegenerative disorder.

21. A method according to claim 20 wherein said neurodegenerative disorder is Parkinson's disease.

22. A compound of formula I:

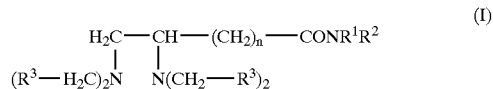

wherein $R^1$ is H or hydrocarbyl; $R^2$ is a hydrophobic radical; $R^3$ is a radical selected from 3-($C_2$–$C_6$)acyl-4-hydroxyphenyl, 3-hydroxyimino($C_2$–$C_6$)alkyl-4-hydroxyphenyl, or COOZ, wherein Z is H, ($C_1$–$C_6$) alkyl, aryl or ar($C_1$–$C_6$)alkyl; and n is an integer from 1 to 20, excluding the compounds:
N-[5-(tert-butoxycarbonyl)pentyl]-4,5-bis[(bis(benzyloxycarbonyl)methyl]amino]valeramide;
N-(3-benzyloxycarbonylaminopropyl)-4,5-bis[di(methoxycarbonylmethyl)amino]valeramide;
N-(3-benzyloxycarbonylaminopropyl)-4,5-bis[di(benzyloxycarbonylmethyl)amino]valeramide; and
N-(benzyloxycarbonylaminoethyl)-4,5-bis[di(carboxylmethyl)amino]valeramide.

23. The compound of claim 22 consisting of N-(3-benzylcarbonylaminopropyl)-4,5-bis[bis(3-(1-hydroxyiminoethyl)-4-hydroxybenzyl)amino]valeramide.

24. A compound of formula II:

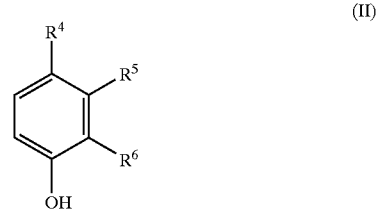

wherein $R^4$ is ($C_1$–$C_6$)acyl, nitro($C_1$–$C_6$)alkyl, cyano($C_1$–$C_6$) alkyl, ($C_1$–$C_6$)alkoxy($C_1$–$C_6$)alkyl or —$CH_2NR^7R^8$, wherein $R^7$ and $R^8$, the same or different, is each H or ($C_1$–$C_6$)alkyl, or together with the N atom form a saturated or unsaturated 5–7 membered ring optionally containing a further heteroatom selected from N, O or S, the further N atom in such saturated 5–7 membered ring being optionally substituted by ($C_1$–$C_6$)-alkyl, ($C_1$–$C_6$)-acyl, hydroxy-($C_1$–$C_6$)alkyl, ($C_{1-C6}$) alkoxycarbonyl, and 8-hydroxyquinolin-5-yl-($C_1$–$C_6$) alkyl, and $R^5$ is H and $R^6$ is ($C_2$–$C_6$)-acyl or hydroxyimino($C_2$–$C_6$) alkyl, excluding the compounds:

2-hydroxy-5-(dipropylaminomethyl)acetophenone; and 2-hydroxy-5-(dipropylaminomethyl)acetophenone oxime.

25. A compound of formula II:

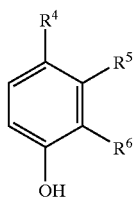

wherein

R$^4$ is (C$_1$–C$_6$)acyl, nitro(C$_1$–C$_6$)alkyl, cyano(C$_1$–C$_6$)alkyl, (C$_1$–C$_6$)alkoxy(C$_1$–C$_6$)alkyl or —CH$_2$NR$^7$R$^8$, wherein R$^7$ and R$^8$, the same or different, is each H or (C$_1$–C$_6$)alkyl, or together with the N atom form a saturated or unsaturated 5–7 membered ring optionally containing a further heteroatom selected from N, O or S, the further N atom in such saturated 5–7 membered ring being optionally substituted by (C$_1$–C$_6$)-alkyl, (C$_1$–C$_6$)-acyl, hydroxy-(C$_1$–C$_6$)alkyl, (C$_1$–C$_6$)alkoxycarbonyl, and 8-hydroxyquinolin-5-yl-(C$_1$–C$_6$)alkyl, and R$^5$ and R$^6$ together with the phenyl ring form a quinoline, a 1,2,3,4-tetrahydroquinoline or a perhydroquinoline ring, excluding the quinoline compounds wherein R$^4$ is (C$_1$–C$_2$)acyl, cyanomethyl, (C$_1$–C$_6$)alkoxymethyl or —CH$_2$NR$^7$NR$^8$, wherein R$^7$ and R$^8$ are both H or (C$_1$–C$_6$)alkyl, or together with the N atom form a saturated ring selected from the group consisting of pyrrolidino, piperidino, morpholino and piperazino.

26. The compound of claim 25 consisting of 5-[4-(2-hydroxyethyl)piperazin-1-ylmethyl]-8-hydroxyquinoline.

* * * * *